United States Patent [19]

Coull et al.

[11] Patent Number: 5,011,861

[45] Date of Patent: Apr. 30, 1991

[54] MEMBRANES FOR SOLID PHASE PROTEIN SEQUENCING

[75] Inventors: James M. Coull, Acton; Darryl J. Rappin, North Billerica; Hubert Koester, Concord; Malcolm G. Pluskal, Bedford; Michael J. Steuck, North Reading; Alex G. Bonner, Lexington, all of Mass.

[73] Assignee: Millipore Corporation, Bedford, Mass.

[21] Appl. No.: 212,430

[22] Filed: Jun. 28, 1988

[51] Int. Cl.$^5$ .............................................. C08G 18/14
[52] U.S. Cl. ......................................... 521/53; 521/54
[58] Field of Search .................................. 521/53, 54

[56] References Cited

U.S. PATENT DOCUMENTS

| | | | |
|---|---|---|---|
| 4,065,412 | 12/1977 | Dreyer | 260/8 |
| 4,224,439 | 9/1980 | Ayers et al. | 536/32 |
| 4,330,440 | 5/1982 | Ayers et al. | 525/54.31 |
| 4,340,482 | 7/1982 | Sternberg | 210/500.24 |
| 4,603,114 | 7/1986 | Hood et al. | 436/89 |
| 4,618,533 | 10/1986 | Steuck | 428/315 |
| 4,704,256 | 11/1987 | Hood et al. | 422/58 |

OTHER PUBLICATIONS

P. Matsudaira, *J. of Biological Chemistry*, 262(1): 10035–10038, (1987).
R. H. Aebersold et al., *J. of Biological Chemistry*, 261(9): 4229–4238 (1986).
S. Kent et al., *BioTechniques;* 5(4):314–321 (1987).
A. J. Dias and T. J. McCarthy, *Macromolecules,* 17:2529–2531 (1984).
H. Kise and H. Ogata, *J. Polymer Science,* 21:3443–3451 (1983).

*Primary Examiner*—Maurice J. Welsh
*Attorney, Agent, or Firm*—Hamilton, Brook, Smith & Reynolds

[57] ABSTRACT

A membrane suitable for immobilizing peptides and proteins is disclosed. The membrane is a flexible, polymeric, porous membrane which contains functional groups capable of covalently linking the peptides and proteins. The functional groups can be provided by reacting the membrane itself or a coating thereon with nucleophiles which provide —$NH_2$, —SH, —OH or —COOH functionality to the membrane surface. Additionally, surfaces containing —$NH_2$ groups can be further reacted with diisothiocyantes to provide an isothiocyanate functionality having enhanced covalent binding characteristics.

16 Claims, 6 Drawing Sheets

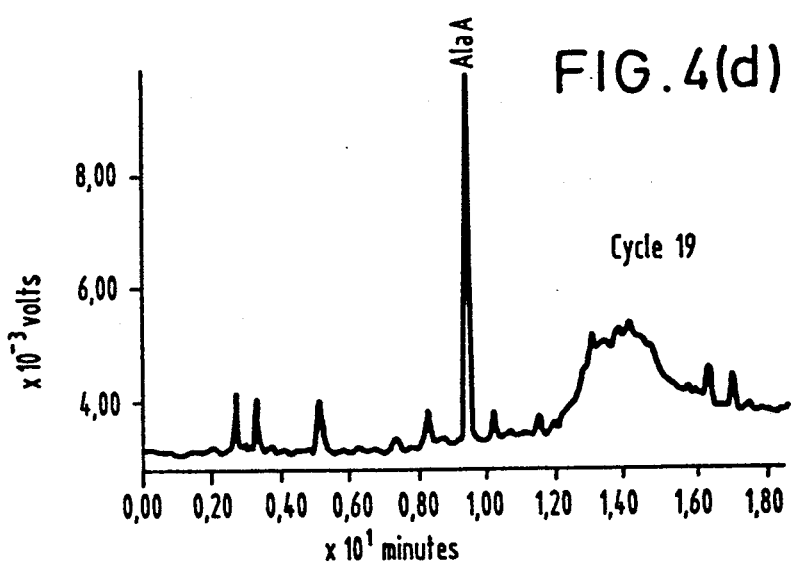
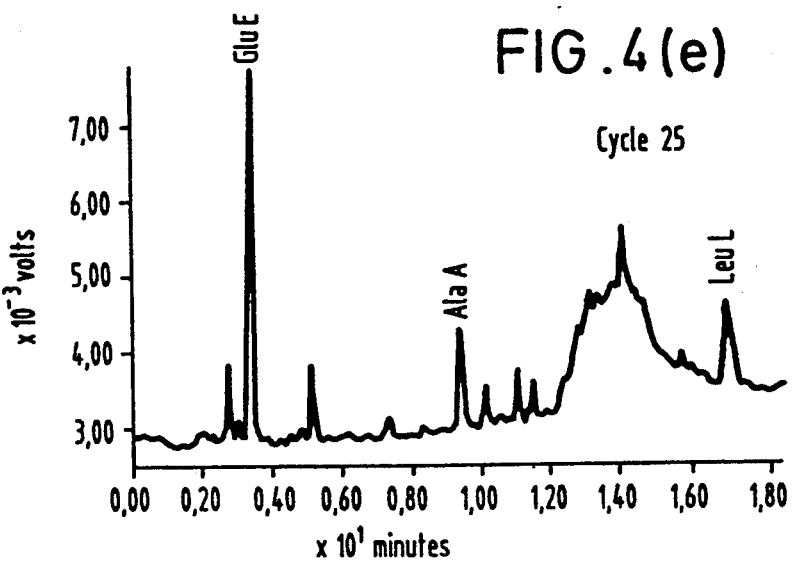
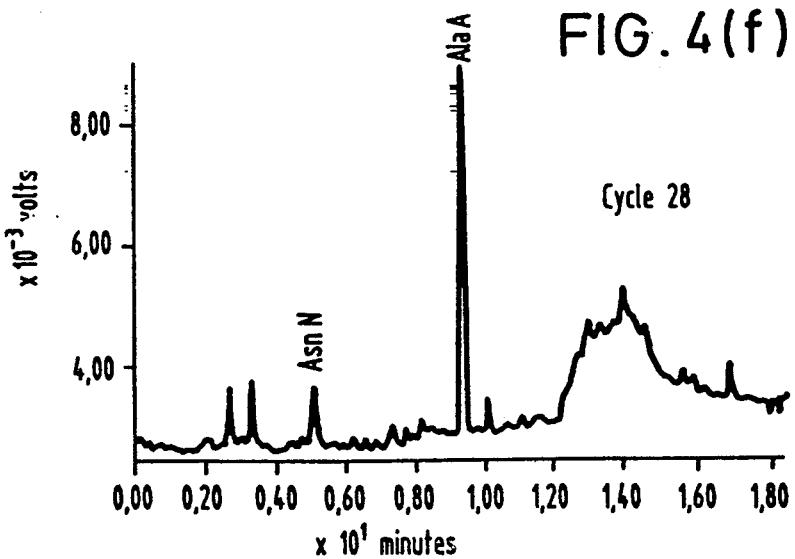

MEMBRANES FOR SOLID PHASE PROTEIN SEQUENCING

FIELD OF THE INVENTION

This invention relates to a material for immobilizing peptides and proteins to allow for their sequence determination by chemical or enzymatic degradation. The materials of this invention covalently bind peptides and proteins and exhibit appropriate physical properties and chemical functionalities optimal for protein sequencing.

BACKGROUND OF THE INVENTION

The determination of the amino acid sequence of proteins is very important for modern molecular biology. Proteins and peptides are essential components of all living cells. They are the structural elements of cell walls and cell membranes, enzymes, immunoglobulins/antibodies, transport molecules and most hormones. The building blocks of proteins are the 20 natural amino acids that are covalently linked together via amide bonds and thus form linear protein chains. The amino acid sequence (primary structure) determines the very complex secondary and tertiary structures responsible for the biological functions of the proteins.

The sequence of a protein or peptide can, in principle, be deciphered by a stepwise chemical or enzymatic degradation from either the amino- (N-) or carboxyl- (C-) terminal end. Single amino acids are removed one by one from the polypeptide chain, separated and identified. Although several methods for a stepwise chemical or enzymatic degradation have been elaborated (see: Elizinga, M. editor, Methods in Protein Sequencing, Humana Press, Clifton, N.J., 1982) the preferred method was introduced by Edman in (*Acta Chem. Scand.*, 4:283 (1950)).

In the method described by Edman, the chemical procedure for removing one amino acid residue from a polypeptide chain consists of three steps. First the polypeptide is reacted at its amino-terminus with an isothiocyanate (ITC), e.g. phenylisothiocyanate (PITC), in a solvent under basic or anhydrous conditions to form a phenylthiocarbamate (PTC). This step is generally referred to as "coupling". Second, under the influence of anhydrous acid (e.g., trifluoroacetic acid, TFA), the PTC cyclizes to an anilinothiazolinone (ATZ) with concomitant cleavage of the last N-terminal amino acid from the polypeptide chain. This step is generally referred to as "cleavage". This provides exposure of the amino groups of the next, adjacent amino acid in the polypeptide chain for the following reaction cycle. The ATZ derivatives are relatively unstable and therefore, in the third step, are converted to the stable phenylthiohydantoins (PTH) by treatment with aqueous acid (e.g., TFA). This step is generally referred to as "conversion". The chemistry of one cycle is shown in the reactions below.

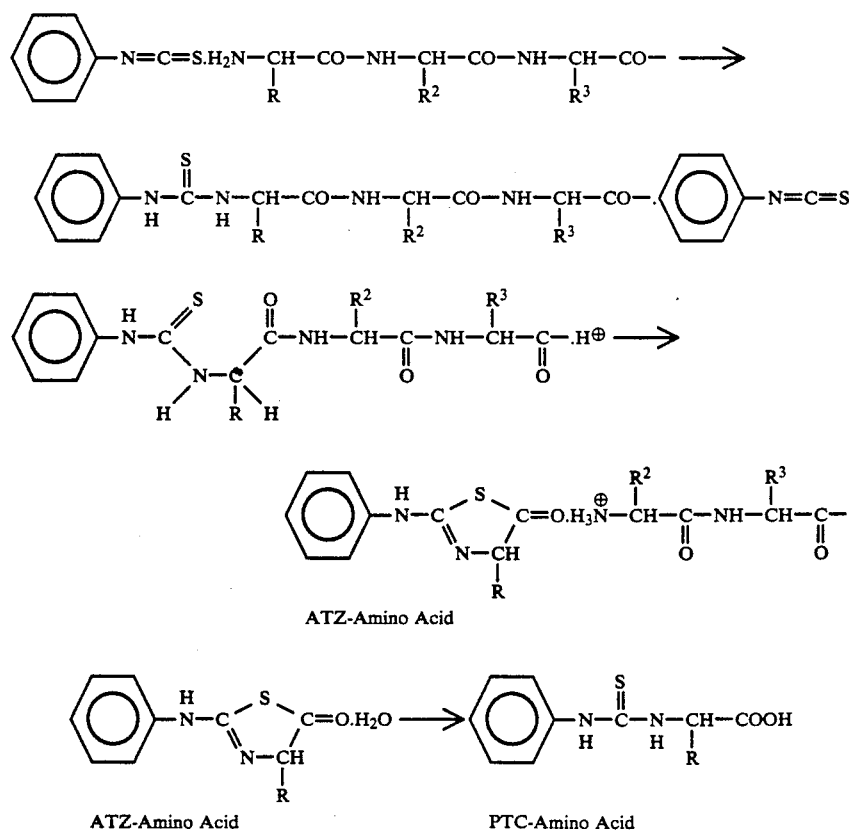

-continued

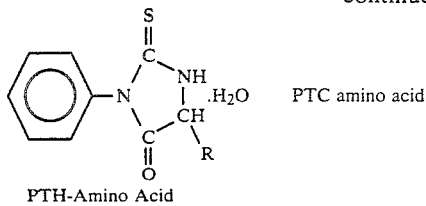

PTC amino acid

PTH-Amino Acid

Conditions have been determined for separating the 20 PTH derivatives of the natural amino acids of high performance liquid chromatography (HPLC). Due to the specific retention times of the 20 PTH amino acid derivatives, the amino acid being removed by each respective cycle can be identified.

The polypeptide, which is shortened by one amino acid, is subjected to the next degradation cycle to furnish the second amino acid derivative in the sequence. The sequence is determined by repeating the foregoing steps for each of the amino acids in the polypeptide chain.

Several variations of the Edman chemistry have been proposed: The 'liquid phase method' described above has been automated as a 'spinning cup automatic sequencer' (Edman, P. and Begg, G., *Eur. J. Biochem.*, 1:80 (1967) and U.S. Pat. No. 3,725,010).

The first use of solid supports in Edman peptide sequencing was described by Schroeder in *Methods in Enzymology*, 11:455 (1967). In this method, the peptide or protein was applied to a paper strip. The material remained adsorbed to the paper, without the formation of covalent bonds, throughout the sequencing process. Coupling and cleavage were performed by exposing the paper strip and adsorbed polypeptide to gas phase reagents. As such, this process is referred to as gas phase sequencing. The process has been automated as described by Hewick, R.M. et al. in *J. Biol. Chem.*, 256:7990 (1981). Unfortunately, this method worked satisfactorily only for proteins which remained insoluble on the surface of the paper strip during the sequencing reactions. The method therefore had to be performed under very controlled conditions.

As a result of the above limitations, the solvents used in the sequencing must be volatile and carefully selected to allow quantitative removal of reagents after the coupling step. To maximize the signal, cleavage and transfer of the ATZ derivatives must be performed without elution of any of the protein from the solid support. Additionally, all solvents and reagents used must be very pure, since they could only be removed from the paper surface by drying/evaporation. Any remaining non-volatile impurities might interfere with subsequent determination of PTH derivatives.

Unfortunately, cycle time for the sequencing is often long, since reactions in the gas phase are slow. This may be because contact of reagents with the protein is mediated only by convection. Due to the fact that the process employs gas-phase reagents, agitation and/or the use of liquid solvents that would promote fast reaction rates, complete extraction of reagents, and removal of ATZ derivatives is not possible. In addition, the solubility of the 20 ATZ and PTH derivatives differs significantly due to the different properties of the 20 distinct amino acid side chains. The efficient removal of the derivatives from the solid support without loss of non-covalently bound protein is therefore difficult.

Thus, sequence data can only be obtained by compromising reaction conditions. This leads to long reaction times and also results in inefficient reactions and solvent extractions. Consequently, only relatively short peptides can be sequenced by this method. Furthermore, the gas phase sequencing method is not suitable for high sensitivity sequencing of small amounts of protein (in the picomol range).

Although the gas phase sequencing method has been significantly improved by the adsorption of proteins to Polybrene-coated (Polybrene is a trademark of Abbott Laboratories) glass fiber filters (Hewick, R.M. et al., *J. Biol. Chem.*, 256:7990 (1981) and Tarr, G.E. et al., *Anal. Biochem.*, 84:622 (1978)), there are still serious drawbacks. For example, the Polybrene-coated glass fiber filter has to be extracted by performing 3 to 5 degradation cycles before sample application. This precycling reduces the background of some impurities to a practical level, but several UV-absorbing contaminants remain which interfere with coeluting PTH derivatives during HPLC separation and identification. This results in unpredictable and relatively low initial yields: for sperm whale myoglobin, for example, initial yields of 25% (Esch, F.S., *Anal. Biochem.*, 136:39 (1984)) and 78% (Hawke, D.H. et al., *Anal. Biochem.*, 147:315 (1985)) have been reported. In addition to this, the other previously mentioned disadvantages still apply. These disadvantages result from compromises to prevent a wash-out of the non-covalently trapped polypeptide. Due to the numerous dry-down steps to remove solvents and reagents, impurities are concentrated onto the surface, necessitating the use of ultrapure reagents and solvents.

The covalent attachment of 3-aminopropyl or N,N,N-trimethylammoniumpropyl groups to glass fiber filters has improved the situation to some extent, in that precycling is not necessary and initial yields of PTH amino acid derivatives are higher (Aebersold, R.H. et al, *J. Biol. Chem.*, 261:4229 (1986)). The background level has also been significantly lowered due to the strong electrostatic immobilization of the proteins on the glass fiber surface.

In a recent patent (U.S. Pat. No. 4,665,037) a liquid-solid affinity chromatography which solves some of the aforementioned problems is described. However, no protein sequencing results are given to demonstrate the utility of the method. Additionally, the various affinity supports and reagents are difficult to synthesize and automation of this process appears to be difficult. Furthermore, in the process described, the peptides and proteins have to be chemically modified prior to the sequencing process to block some side chain functionalities which otherwise would interfere with the affinity reagents.

Most of the disadvantages of the previous methods and materials result from the non-covalent nature of the immobilization of the polypeptides onto the solid support. Covalent attachment of proteins and peptides to the solid support should allow for a superior sequencing procedure to be employed. This procedure is referred to as solid phase sequencing.

Two sets of problems have to be addressed for solid phase sequencing to be practical:
(1) the choice of polymer support and
(2) the method of covalent immobilization to the support.

Various supports have been used in conjunction with Edman protein sequencing chemistry.

For example, several porous solid supports have been based upon a polystyrene backbone having functionalized phenyl groups. Representative reactions for the conversion of the phenyl group containing materials to useful solid phase sequencing supports are given below:

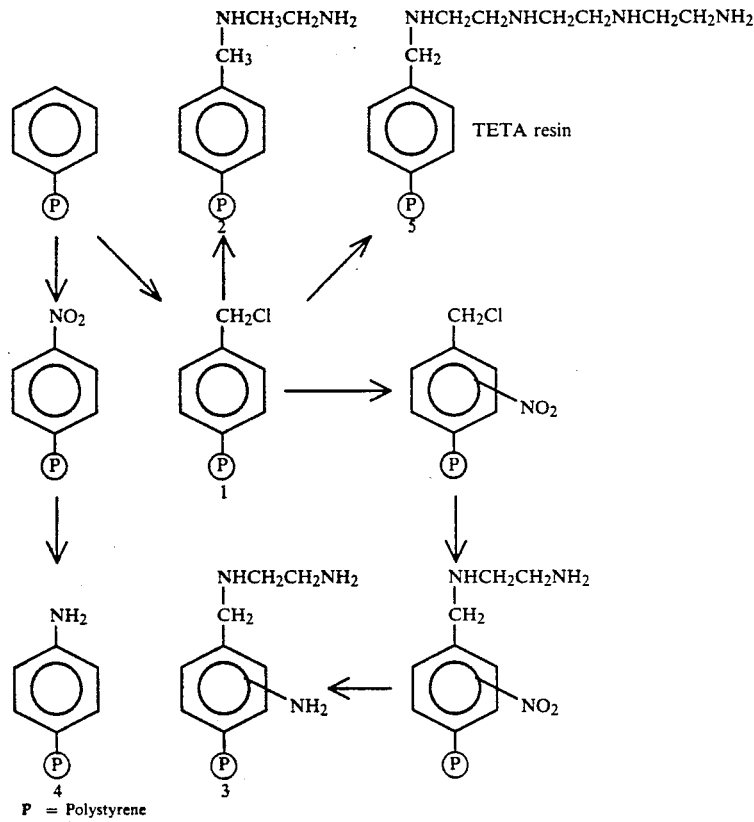

P = Polystyrene

In the first reaction above, polystyrene having phenyl groups has been functionalized with chloromethyl groups to form material (1). This is then transformed by treatment with ethylenediamine to (2-aminoethyl)-aminomethyl polystyrene designated resin (2). (Laursen, R.A., *Eur. J. Biochem.*, 20:89 (1971). Although peptides could be attached in high yields to this support, sequence overlaps were significant due to incomplete cleavage in the TFA step because of poor penetration of the acid into the hydrophobic polymer. Addition of an amino group to the backbone phenyl ring to give resin (3) resulted in greatly improved swelling in TFA (Laursen, R.A. et al, *FEBS Letters*, 21:67 (1972)). Under the acidic conditions provided by TFA the amino groups are protonated and thus the polarity of the resin is increased.

Further development of the diisothiocyanate attachment method is described by Laursen et al. in *FEBS Lett.*, 21:67 (1972). Aminopolystyrene resin (4) was demonstrated to be equally satisfactory as resin (3) for peptide attachment. Preparation of (4) was much easier than (3), so it rapidly became the resin of choice for this method of attachment. However, aminopolystyrene resin proved to be less efficient for the immobilization of peptides by certain carboxyl activation chemistries due to the relatively poor nucleophilicity of aryl amines.

Horn and Laursen in *FEBS Letters*, 36:285 (1973)) developed the triethylenetetramine (TETA) resin (5) which showed many of the desirable properties of (3) with the added attraction of much simpler synthesis. The long chain aliphatic amino groups were also much more accessible to reagents as well as peptides and proteins Some stability problems, however, were noted after a few months of storage, even under refrigeration.

Although used successfully in much of the early work in solid-phase protein sequencing, the polystyrene-based resins exhibit several inherent properties which increase the difficulty of both preparation and use. For example, the degree of both substitution and crosslinking must be carefully controlled. Most of the successful resins were derived from resins crosslinked with 1-2% divinylbenzene (Merrifield resin). Greater degrees of crosslinking resulted in resins with drastically reduced reagent permeability. Chloromethyl substitutions of around 15% were found most practicable; increasing this level simply resulted in increased crosslinking of methylene bridges (Patterson, J.A., in 'Biochemical Aspects of Reactions on Solid Supports', Stark, G.R., editor, Academic Press, New York, 1971, pp. 189).

Solvent-induced swelling of the resins in certain solvents (such as pyridine or TFA) followed by shrinkage in others (e.g., methanol) during a typical Edman degradation cycle resulted in considerable problems due to blockage and solvent channeling when the resin was packed directly in reaction columns. This problem was partly resolved by Laursen (see Laursen, *Eur. J. Biochem.*, 20:89 (1971)) by mixing the resin with a fifty-fold excess of glass beads prior to column packing. This allowed for swelling to occur harmlessly in the interstices between the beads. The issue was addressed more directly by Inman et al. (in 'Solid Phase Methods in Protein Sequence Analysis', Previero, A. and Coletti-Previero, M.A., editors, North Holland Press, Amsterdam, 1978, pp 81) who prepared resins derived from highly crosslinked polystyrene. The resulting material was largely incompressible, was very resistant to solvent-induced volume changes and possessed a large reagent-accessible surface area.

One further deficiency of the earlier polystyrene resins was that the matrix did not permit penetration of large proteins or peptides. The practical limit for efficient attachment was generally held to the peptides of only 30–50 residues in length (Laursen, R.A. and Machleidt, W., 'Methods of Biochemical Analysis', Glic,, D., editor, 26, pp 201 (1980).

In addition to the polystyrene resins, polyacrylamide supports have also been used for solid-phase sequencing. Representative reactions with polyacrylamides are given below:

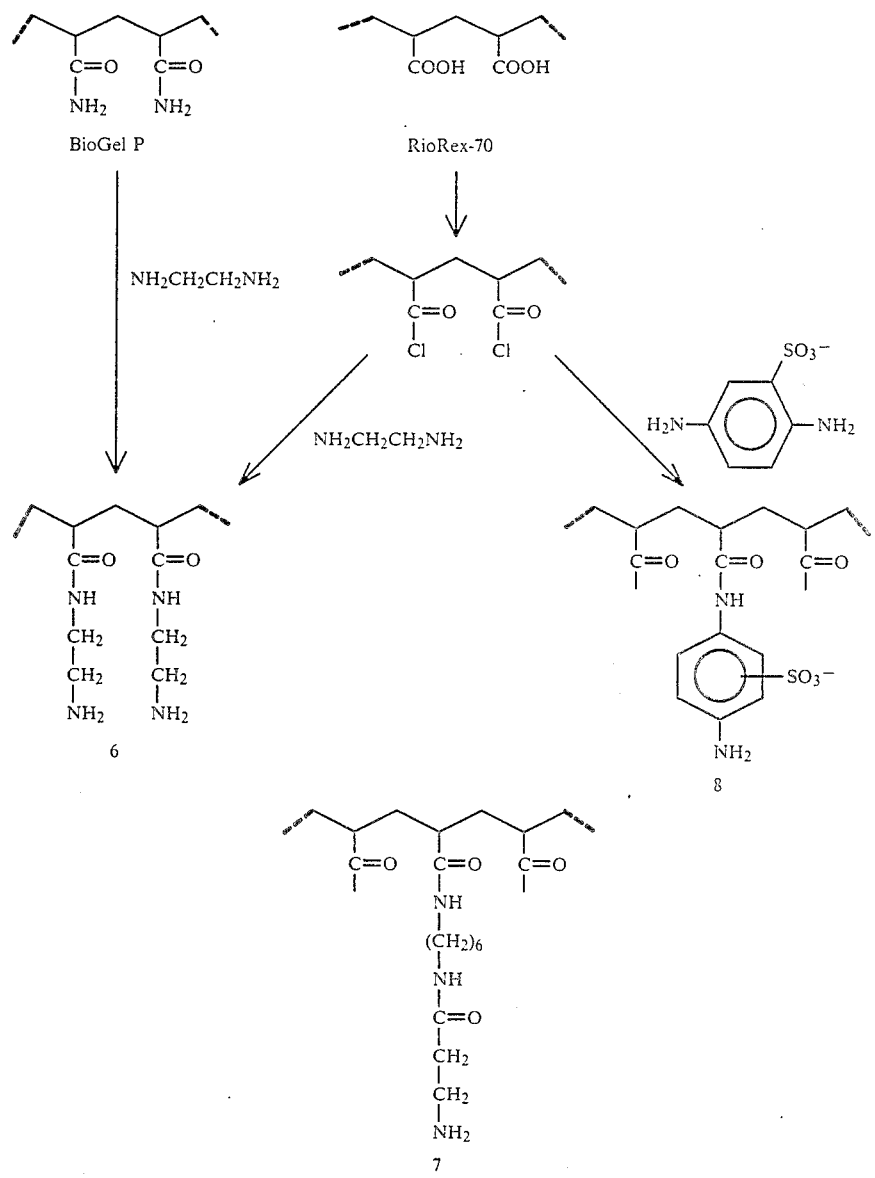

Early experiments resulted in a hydrophilic sequencing resin (6) prepared from polyacrylamide beads (Bio-Gel P, Bio-Rad Laboratories) and ethylenediamine. Cavadore et al., *FEBS Letters*, 66:155 (1976), prepared and used a resin similar to (6) from Bio-Rex 70 (a weak cation exchanger) by conversion to the acid chloride followed by reaction with ethylenediamine. Cavadore and Vallet, *Anal. Biochem.*, 84:402 (1978), prepared another hydrophilic activated polyacrylamide (8) by coupling 1,4-diaminobenzene sulphonic acid to polyacrylyl chloride. Subsequently, the free arylamino groups were converted to isothiocyanate in situ. The sulphonic acid residues imparted hydrophilic character to the resin and increased non-covalent protein binding by ion-exchange.

Atherton et al., *FEBS Letters*, 64:173 (1976) also prepared a polyacrylamide support with a beta-alanylhexamethylendiamine side chain (7) which was used as a sequencing support when mixed with glass beads to overcome flow problems.

Although capable of binding larger peptides and proteins than the earlier polystyrene supports, the polyacrylamide-based resins still suffered from significant flow problems. These resulted from solvent-induced swelling and shrinking of the supports which caused blockage of the fluid flow pathways. The resins were sensitive to prolonged, repeated exposure to TFA which resulted in increased levels of contamination eluting from the columns after several sequencing cycles. After some initial interest, none of the above polyacrylamide resins have been used extensively in sequencing (Laursen, R.A. and Machleidt, W., 'Methods of Biochemical Analysis', Glick, D., ed., 26, pp. 201 (1980)).

Largely because of the poor properties and limited accessible surface area of the polymeric supports mentioned above, by far the most successful supports for solid-phase sequencing have been prepared by the derivatization of controlled pore glass (CPG) with alkylsilanes (see Machleidt, W. and Wachter, E., *Methods in Enzymol.*, 47:263 (1977)). A variety of supports based on these materials are shown below:

nominal pore size of 75 Å was held to be suitable for most solid-phase sequencing applications (Laursen, R.A. and Machleidt, W. (1980), see above) although more efficient attachment of larger proteins (greater than about 30,000 daltons) or proteins in the presence of detergents could be achieved using CPG supports of up to 500 Å nominal pore size (e.g., Bridgen, J., *Methods in Enzymol.*, 47:321 (1977)).

The principal superiority of solid-phase protein sequencing comes mainly from the greater flexibility in the choice of conditions for the sequencing chemistries. However, solid-phase protein sequencing in the past was severely restricted because efficient methods to immobilize peptides and proteins on the solid support were not available, particularly when working with very small amounts.

A number of methods have been employed: Horn and Laursen, *FEBS Letters*, 36:285 (1973), immobilized homoserine lactone terminated fragments obtained after cyanogen bromide cleavage of proteins to amino supports. L'Italien and Strickler, *Anal. Biochem.*, 127:198 (1982) have used water-soluble carbodiimides to selectively covalently attach peptides through their alpha-carboxyl groups to amino supports. The attachment of

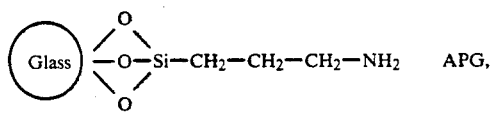 9

APG,

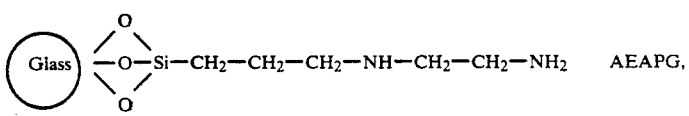 10

AEAPG,

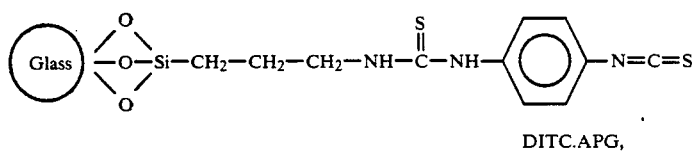 11

DITC.APG,

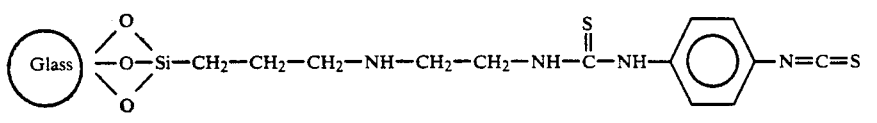 12

DITC.AEAPG,

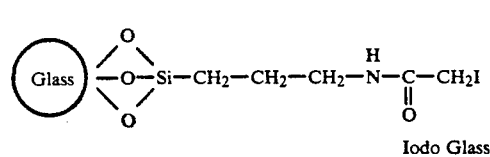 13

Iodo Glass

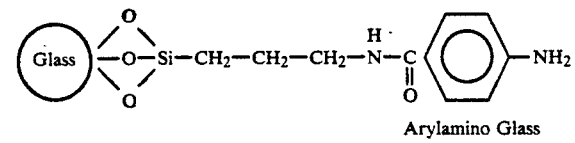 14

Arylamino Glass

Two types of CPG supports have been used extensively: 3-aminopropyl glass (APG), designated (9), prepared by reaction of CPG with 3-aminopropyl triethoxysilane (Robinson, P.J. et al., *Biochim. Biophys. Acta*, 242:659 (1971); Wachter, E. et al., *FEBS Letters*, 35:97 (1973)) and N-(2-aminoethyl)-3-aminopropyl glass (AEAPG), (10), obtained by reaction of CPG with the corresponding trimethoxy silane (Bridgen, J., *FEBS Letters*, 50:159 (1975)). Controlled pore glass with a peptides through their tyrosine side chains using diazophenyl supports has been investigated by Chang et al., *FEBS Letters*, 84:187 (1977). The two amino-functional supports APG (9) and AEAPG (10) have also served as precursors to link peptides or proteins to the solid support via the sulfhydryl groups of cysteine residues. This was accomplished by reacting APG with iodoacetic acid in the presence of dicyclohexylcarbodiimide (DCCI) to produce the iodo-glass support (13). Little or no side reaction was observed with the hydroxyl groups of serine, threonine and tyrosine or with methionine (Chang, J.Y. et al., *FEBS Letters,* 78:147 (1977)). An aryl amino support (14) was prepared by reaction of APG (9) with p-nitrobenzoyl chloride followed by reduction to the aryl amine with sodium dithionite (Weetall, H.H., *Biochim. Biophys. Acta,* 212:1 (1970). This support has proven to be particularly suitable for attachment of peptides following activation of carboxyl functions with carbodiimides. A review describes the various methods of attachment in more detail (Laursen and Machleidt 'Methods of Biochemical Analysis', Glick, D., ed., 26, pp. 201 (1980)).

By far the most widely used method to attach peptides and proteins to solid supports involves the epsilon amino group of lysine residues with activated isothiocyanate supports such as (11) or (12). These supports are prepared by reaction of either APG (9) or AEAPG (10) with p-phenylene-1,4-diisothiocyanate (DITC) (Wachter, E. et al. (1973)). Reaction of the amino groups of proteins with the isothiocyanate moiety is readily achieved in mildly basic aqueous solution (pH 8) at temperatures from 25-55° C. The presence of detergents (e.g., sodium dodecyl sulphate (SDS)), or chaotropic agents such as 8M urea or saturated guanidinium hydrochloride have no significant effect on the attachment chemistry (Machleidt, W. et al., 'Advanced Methods in Protein Sequence Analysis', Wittmann-Liebold, B., Salnikow, J. and Erdmann, V.A., editors, Springer-Verlag, Berlin, Heidelberg, pp. 91 (1986). Consequently, attachment of proteins or peptides to DITC supports is generally accepted as the method of choice for solid-phase sequence analysis.

The advantages of CPG supports over the earlier polymeric resins are numerous. The very large surface area per unit weight (typically 100 square meter/g for 200-400 mesh CPG of 200 Å nominal average pore-size) greatly improves the attachment capacities for proteins and peptides (capacities of 0.2 mmol amine/g support are typical; Schmitt, H.W. and Walker, J.E., *FEBS Letters,* 81:403 (1977)). The functional groups on the porous glass supports are accessible to solvents of all kinds and the rigid inorganic matrix is incompressible for all practical purposes Supports prepared from 200-400 mesh CPG beads provide an efficient packing of continuous-flow reaction columns, with very low fluid back-pressure.

The coupling medium can be freely selected according to the solubility of peptides and proteins and the requirements of the coupling chemistries: for example, the hydrophobic DCCD-binding subunit of mitochondrial ATP-ase was attached to DITC activated APG (11) in a mixture of chloroform and methanol (Wachter, E. and Weerhahn, R., 'Solid-Phase Methods in Protein Sequence Analysis', Previero, A. and Coletti-Previero, M.A., editors, North Holland Press, Amsterdam, pp. 185 (1978)).

The porous glass beads can be used in reaction columns with aqueous as well as anhydrous organic solvents. The physical stability of the glass beads has facilitated the design of efficient Edman degradation chemistries (Walker, J.E., et al., *Biochem. J.,* 237:73 (1986)) with significant improvements in speed and repetitive stepwise yields.

Apart from slight problems with slow hydrolytic loss of surface siloxane groups at the elevated temperatures (up to 56.C) and basic conditions (pH 10-11) required for part of the typical Edman degradation (perhaps losing up to 0.5% of attached peptide per cycle), the principle disadvantages to the use of glass beads for solid-phase sequence analysis are related to the practical problems of sample preparation (coupling of the peptide or protein) and handling.

A typical series of steps involved in sample preparation is as follows:

(1) The protein or peptide is dissolved in 0.2-0.8 ml 50 mM sodium bicarbonate buffer pH 8.0 (perhaps containing 1-2% w/v SDS to aid solubility) and the solution added to 10-100 mg DITC APG (11).

(2) Following incubation for 2-4 hr at 40-50° C., 0.2 ml n-propylamine is added to block excess isothiocyanate groups on the support.

(3) The glass/protein suspension is then centrifuged and the supernatant (containing any unbound peptide) is recovered.

(4) The glass beads are then transferred to a small fritted filter funnel and washed with bicarbonate and methanol (containing traces of triethylamine, TEA).

(5) The washed support is then dried by applying light vacuum for a few minutes, and packed dry into the sequencer reaction column.

Similar techniques are used for the polystyrene-based supports described previously. In each case, these procedures require careful attention and manipulative skills, particularly when working with small quantities of beads (typically less than 10 mg).

The use of beaded supports (either CPG or polystyrene resin) also precludes the use of electroblotting techniques for the recovery of proteins from SDS polyacrylamide gels, which require the transfer onto a sheet or membrane support.

While the above materials and methods for sequencing peptides and proteins have been quite valuable, many of them are unable to meet the current requirements in molecular biology. Recent developments in this field demand the determination of protein and peptide sequences in the picomol range and below. This is because many proteins of great biological interest can only be obtained in these small quantities. Establishing a short peptide sequence at the N-terminus of a protein enables one to initiate experiments aimed at identifying the corresponding gene and generating the entire protein sequence by determining the DNA sequence. Complex protein patterns from normal cells or cells derived from various diseased tissues (such as cancer, degenerative nervous diseases (Harrington, M.G. and Merrill, C.R., *Clinical Chemistry,* 30:1933 (1984)) and genetic diseases) can be visualized by isolating proteins in 1-10 nanogram quantities using 2D polyacrylamide gel electrophoresis (O'Farell, P.H., *J. biol. Chem.,* 250:4007 (1975). To obtain sequence information from such rare proteins does not allow the type of sample manipulation described above for the beaded supports. The availability of a flat support onto which the respective proteins can be directly blotted after ID and 2D polyacrylamide gel electrophoresis is a necessity. Additionally, efficient methods to covalently immobilize these very small amounts of proteins onto the flat support during the blotting process are needed as well. Thus isolation of proteins by electroelution from polyacrylamide gel pieces or by HPLC methods, (which are laborious and very often result in very low recovery yields), can be avoided.

Aebersold et al., *J. Biol. Chem.*, 261:4229 (1986); Kent, S. et al., *BioTechniques*, 5:314 (1987); Vandekerckhove, J. et al, *Eur. J. Biochem.*, 152:9 (1985) derivatized the surface of glass-fiber sheets with 3-aminopropyl trimethoxy silane and from this prepared the activated isothiocyanate surface by reaction with a DITC analog to form glass-fiber (11). The DITC glass-fiber sheets were successfully used to covalently attach and sequence proteins electroblotted directly from SDS polyacrylamide gels (Aebersold et al., (1986), see above). Significant drawbacks of glass-fiber papers are the difficulties of detecting proteins using the popular Coomassie Blue for staining (Aebersold et al. (1986), see above), the non-optimal texture which does not allow for an intimate contact and undistorted transfer of material during the blotting process, the very low capacity to bind proteins, (which is in the range of 7-10 ug per $cm^2$), and the fact that both the repetitive yield and initial yield for coupling of proteins electroblotted onto glass-fiber sheets decreases with the decreasing amount of proteins present (Yuen, S. et al., *Applied Biosystems User Bulletin*, 24 Foster City, CA (1986)).

As the coupling reaction between the peptides or proteins and the ITC group on the surface of the glass fiber paper is slow, a trapping process for the peptides or proteins would increase the efficiency of coupling; DITC-glass fiber paper can provide this only by electrostatic interaction with the amino groups which were left over following the reaction with DITC. As there could be also a repulsion operating between the ammonium groups on the glass fiber surface and similarly charged groups on the surface of the peptide or protein this is an unpredictable, variable and inefficient process. It is obvious that DITC-glass fiber sheets are particularly inefficient in coupling small peptides and apparently are not suitable for protein sequencing in the picomol range and below.

Other flat materials which provide for a more efficient electroblotting of proteins are nitrocellulose (Towbin, H. et al., *Proc. Natl. Acad. Sci. USA*, 76:4350 (1979)), diazophenyl paper (Renart, J. et al., *Proc. Natl. Acad. Sci. USA*, 76:3116 (1979) and charge-modified nylon sheets (Gershoni, J.M. and Palade, G.E., *Anal. Biochem.*, 124:396 (1982). Nitrocellulose has not been functionalized to allow for covalent attachment of proteins and, in addition, dissolves during a variety of sequencing reactions. When subjected to the Edman degradation chemistry, the charge-modified nylon collapses into a solid pellet, while diazophenyl paper is physically and chemically not stable enough to withstand the repeated cycling associated with the sequencing method. Diazophenyl paper also limits the attachment of a protein to cases in which relatively rare tyrosine residues are present.

Recently, polyvinylidene difluoride (PVDF; also known in the art as polyvinylene fluoride (PVF)) membranes have been used for efficient electroblotting and gas-phase sequencing (Matsudaira, P., *J. Biol. Chem.*, 262:10035 (1987); Pluskal, M.G. et al., *BioTechniques*, 4:272 (1986)). Compared to glass fiber sheets derivatized with ammonium groups, the capacity of PVDF membranes to bind proteins is significantly better (170 ug/$cm^2$ for PVDF versus 7-25 ug/$cm^2$ for derivatized glass fiber sheets; see Matsudaira, 1987). The initial sequencing yield for proteins adsorbed to PVDF (76-97%) also compared very favorably with the 15-25% initial yields obtained for proteins electroblotted onto glass fiber sheets (Matsudaira, 1987, see above).

The very efficient and high adsorption properties of PVDF membranes for proteins has several other advantages. Protein solutions can be rapidly desalted by dot-blotting onto the membrane surface and washing with water to remove buffer salts. In addition to this, dilute protein samples can be concentrated several fold on the membrane surface through multiple loadings.

PVDF has been used for direct gas phase protein sequencing (Matsudaira, *J. Biol. Chem.*, 262:10035 (1987). The mechanism of protein adsorption to PVDF is not known, but may result from hydrophobic or dipole interaction between proteins and the polymer surface. Thus, the disadvantages described above, resulting from non-covalent attachment of peptides and proteins to a solid support, apply to PVDF as well.

U.S. Pat. No. 4,340,482 describes a process for grafting amino acid molecules under highly basic conditions onto the surface of the preformed PVDF membrane. Apparently under strong basic conditions (particularly in the presence of a phase transfer catalyst) hydrogen fluoride is eliminated and carbon double bonds are formed exclusively on the surface of the PVDF membrane (Dias, A.J. et al, *Macromolecules*, 17:2529 (1984). The reaction of amines with fluorocarbon polymers was also described by Bro in *J. Appl. Polymer Sci.*, 1:310 (1959)). Bro suggests that under the influence of the amine, hydrogen fluoride (HF) is eliminated followed by an addition of the amine to the double bond. Several reactions may follow including cross-linking and the elimination of another HF molecule at the addition site of the first amine to form an imino structure which can tautomerize to an enamine structure (Smith, J.R. et al., *J. Appl. Polymer Sci.*, 5:460 (1961)). Aqueous KOH is apparently significantly less reactive to eliminate HF than amines (Chambers, R.D. et al., *Tetrahedron Letters*, 10:629 (1963).

The process described in U.S. Pat. No. 4,340,482, by which amino acids are apparently linked covalently via their amino functions to the surface of PVDF renders the hydrophobic PVDF surface hydrophilic. A different way to modify the properties of a polymer surface is described in U.S. Pat. 4,618,533. In this patent, a permanent coating is grafted and/or deposited onto the surface of a membrane by the copolymerization of appropriate monomers onto all the solvent-accessible surface area of the microporous structure. If monomers such as hydroxypropylacrylate are used as the coating, a hydrophobic surface can be transformed into a hydrophilic surface.

In co-pending U.S. Pat. application Ser. No. 093,011, filed Step. 4, 1987 now U.S. Pat. No. 4,923,901 (Koester, H. and Coull, J.H., entitled 'Membranes with Bound Oligonucletides and Peptides') chemically derivatized membranes linked to protected nucleosides or amino acids are described. These membranes are useful for the synthesis of nucleic acids and peptides.

SUMMARY OF THE INVENTION

The present invention describes polymeric supports suitable for the efficient covalent attachment of peptides and proteins and for solid-phase protein sequencing. The polymeric supports are microporous membranes forming thin, flat, flexible sheets which have a uniform continuous porous structure and functional groups on the solvent-accessible surface area that can react with peptides and proteins to form covalent bonds. The membrane surface can bear a single type of functionality or a mixture of different functionalities to provide a membrane surface having chemical reactivity toward one or several different functional groups in the amino acid side chains of the peptides and proteins. Depending on the functionality of the membrane surface, the reactivity of the membrane to specific functional groups on the protein can be defined.

The overall chemical properties of the derivatized membrane can be either hydrophobic or hydrophilic depending on the particular type of polymer, the presence of coating materials and the functional groups on the membrane surface.

The derivatized membranes of this invention offer a number of distinct advantages over the solid supports previously used for solid phase protein sequencing. For example, the large surface area that results from the microporous structure of the membrane surface allows for a very efficient covalent coupling of proteins and peptides to the solid phase.

Additionally, because the material is a flat, flexible membrane, the covalent coupling can be performed during a blotting in which a protein or peptide is transferred from a separatory gel (for example a one- or two-dimensional polyacrylamide electrophoretic gel), directly onto the membrane surface. Consequently, no further handling, isolation or purification is necessary to prepare the bound proteins or peptides for the sequencing process. By eliminating additional processing steps, significant losses of blotted material can be eliminated.

Furthermore, the flat, flexible structure of the membranes allows them to be formed in various configurations (for example, by rolling), or cut to virtually any shape. Additionally, because the present membranes simplify the immobilization process and are physically and chemically versatile, they are well-suited for use in automated sequencing systems.

The protein bands or spots transferred onto the membrane can be detected by conventional staining procedures using, for example, Coomassie Blue, silver staining, or radiolabelling. After blotting, the protein containing areas of the membrane can simply be cut out and subjected directly to the sequencing procedure. Alternately, if large quantities of the purified peptides or proteins are available, the material can be directly spotted onto the membrane.

Since the peptides or proteins are linked to the membrane by covalent bonds, a variety of solvent or reagent conditions can be used for the sequencing reactions. These include intensive intercycle washing to minimize impurities and reduce background signals on the membrane, as well as fast reaction conditions due to flow-through of reagents. Thus, the present derivatized membranes allow a solid phase protein sequencing system to achieve fast cycle times and high sensitivity. This results from very efficient protein-to-membrane coupling even when the proteins are present in picomole amounts. By selecting materials which are resistant to both acidic and basic conditions, the membranes of this invention are not limited to use in a specific protein sequencing process, but rather have utility for a wide range of different chemical or enzymatic sequencing processes. These processes can be carried out in the solid-, liquid-, or gas-phase or in multi-phase combinations thereof and can use solvents and reagents with a wide range of pH values.

DESCRIPTION OF THE PREFERRED EMBODIMENTS

Figure 1A:
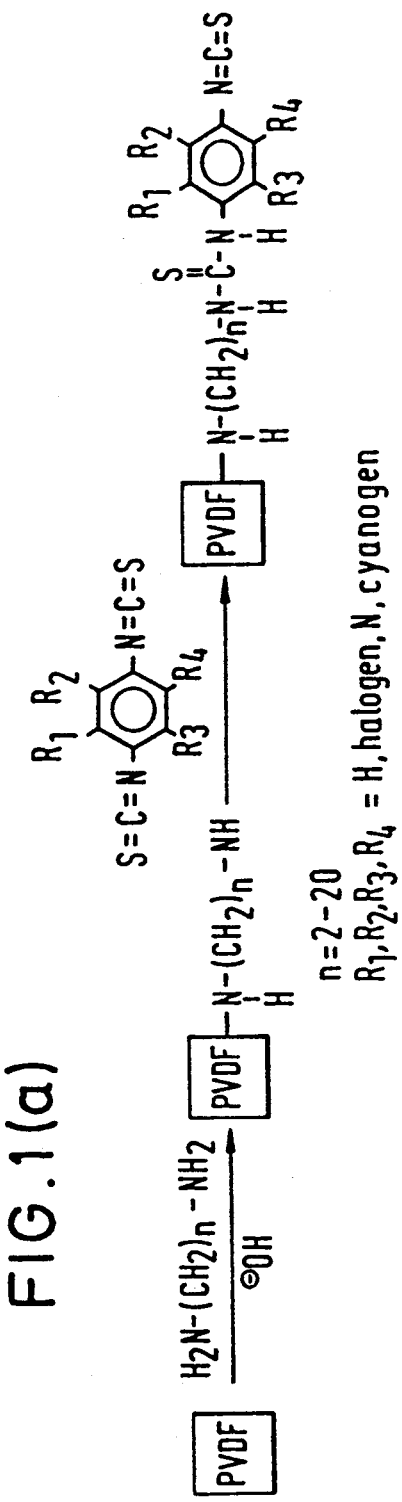
FIG. 1 presents representative formulae for the derivatization of PVDF to provide a membrane suitable for covalently binding peptides and proteins.

The polymeric membranes of this invention are thin, flat, highly flexible membranes having a porous structure. They are capable of covalently binding peptides and proteins and can withstand both chemical and enzymatic protein sequencing processes. The polymeric membranes can be produced by a variety of methods.

In the broadest embodiment, the membrane is a flat, flexible, polymeric composition having a surface capable of covalently binding peptides and proteins. As used herein, the term polymeric composition refers to materials produced from one or more monomer varieties. Representative materials include polyolefins such as polyethylene, polypropylene, polymethylpentene, and the like; polystyrene or substituted polystyrenes; fluorinated polymers such as poly(tetrafluoroethylene), polyvinylidene difluoride, and the like; polysulfones such as polysulfone, polyethersulfone, and the like; polyesters such as polyethylene terephthalate, polybutylene terephthalate, and the like; polyacrylates and polycarbonates; and vinyl polymers such as poly vinyl chloride and polyacrylonitriles. Additionally, copolymers such as copolymers of butadiene and styrene, fluorinated ethylene-propylene copolymer, ethylene-chlorotrifluoroethylene-ethylene copolymer, and the like can be employed as suitable polymeric materials. The preferred polymeric materials are the polymeric fluorocarbons such as polyvinylidene difluoride (PVDF).

The polymeric material should possess a porous structure. In the preferred embodiment, the membrane has an average pore size of between about 0.001 and about 10.0 microns, with an average pore size of between about 0.1 and about 5.0 microns being most preferred. Additionally, at least one section of the membrane should be continuously porous to thereby allow fluid flow through and/or across the membrane.

The membrane can be either coated or uncoated. In the case in which the membrane is coated, the coating is a polymer which preferably covers substantially the entire solvent-accessible surface area of the membrane.

Any monomer or combination of monomers for coating the membrane can be used if the polymerization can be initiated by free radicals and if one of the monomers carries a functionality which directly or after subsequent chemical transformation can be utilized to covalently bind peptides and proteins to the coating on the membrane support. The polymerization of the coating can be carried out before, during or after coating deposition. In the preferred embodiment, the coating is crosslinked, with crosslinking being carried out either during or after coating deposition.

Representative monomers suitable for use as membrane coatings include hydroxyalkyl acrylates or methacrylates such as 1-hydroxypropyl-2-acrylate and -hydroxypropyl-1-acrylate, hydroxypropyl methacryalate, hydroxyethyl methacrylate, 2-amino ethyl methacrylate and the like or mixtures thereof. Other suitable polymerizable monomers include those such as acrylic/methacrylic acid, acrylic/methacrylic acid esters (such as pentafluorophenyl- or 4-nitrophenylesters), 2-N-N-dimethylaminoethyl methacrylate, sulfoethyl methacrylate and the like, and acrylamides, methacrylamides, ethacrylamides and the like.

Suitable polymerization initiators and agents are well known in the art. For a detailed discussion of these and further discussion regarding coated polymers see U.S. Pat. No. 4,618,533 previously described.

The ability of the membrane to covalently bind peptides and proteins is provided by a nucleophile capable of binding to the surface of the membrane or to a coating thereon and also to the peptide or protein itself. In a preferred embodiment, the reactivity of hydrophobic nucleophiles towards a hydrophobic polymeric fluorocarbon, such as the preferred PVDF is exploited.

A wide variety of hydrophobic nucleophiles are suitable for use in derivatization of the polymeric fluorocarbon. In the broadest embodiment, the nucleophiles used in the present invention have the structure:

wherein X is a functional group capable of binding to the membrane or a coating thereon, Y is a functional group capable of covalently binding a peptide or a protein or is capable of being derivatized to covalently bind a peptide or a protein, and N is a linking radical serving to link X and Y. The linking ligand is preferably an alkyl radical, an aralkyl radical having either substituted or unsubstituted phenyl rings, or an aryl radical having substituted or unsubstituted phenyl rings. In the latter two cases, hydrogen substitution can occur at the ortho and/or meta positions of the phenyl ring. Nitrogen, halogens and cyanogens are examples of suitable species for hydrogen substitution, however, this list is not intended to be limiting.

One class of satisfactory nucleophiles are the alpha,omega-substituted amino and/or thio alkanes of the formula:

where n=2-20 and X and Y are as shown below

| X | Y |
|---|---|
| NH$_2$ | NH$_2$ |
| NH$_2$ | SH |
| NH$_2$ | OH |
| NH$_2$ | COOH |
| SH | SH |
| SH | OH |
| SH | COOH |

Preferred nucleophiles of this type include the diamines 1,2-diaminoethane, 1,10-diaminodecane and the dithio 1,6-dithiohexane.

A second class of satisfactory nucleophiles are the aralkylamines and aralkylthiols of the formula below:

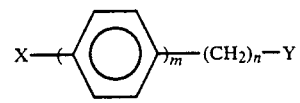

wherein the aryl groups are either unsubstituted or substituted, n=1-20, m=1-3 and X and Y are as shown below:

| X | Y |
|---|---|
| NH$_2$ | NH$_2$ |
| NH$_2$ | SH |
| NH$_2$ | OH |
| NH$_2$ | COOH |
| SH | SH |
| SH | NH$_2$ |
| SH | OH |
| SH | COOH |
| OH | SH |
| OH | NH$_2$ |
| COOH | SH |
| COOH | NH$_2$ |

Preferred nucleophiles of this type include 2-(4-aminophenyl) ethylamine, 2-(4-aminophenyl) phenethylamine, 6-(4-aminophenyl) hexylamine and 1-thio-(4-thiophenyl)ethane.

A third class of satisfactory nucleophiles are the primary or secondary arylamines and arylthiols of the formula below:

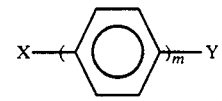

wherein the aryl groups are either unsubstituted or substituted, m=1-3 and X and Y are as shown below:

| X | Y |
|---|---|
| NH$_2$ | NH$_2$ |
| NH$_2$ | SH |
| NH$_2$ | OH |
| NH$_2$ | COOH |
| SH | SH |
| SH | OH |
| SH | COOH |

Preferred nucleophiles of this type include 1,4-diaminobenzene and 1,4-dithiobenzene.

The derivatizing nucleophiles are not intended to be limited to those presented above, however. Rather, a broad range of nucleophiles can be utilized, including but not limited to polymers containing amino groups such as polyvinylamine and compounds with several secondary and/or primary amino functions such as spermine, spermidine and polyethyleneimine. As shown above, compounds having mixed amino and thiol functions on an alkyl, aralkyl or aryl linking ligand are also suitable. Examples of these compounds include 1-amino-2-thioethane (cysteamine), 2-(4-thiophenyl) ethylamine, 2-thio-(4-aminophenyl) ethane and 4-aminothiophenol. The bifunctional compounds with an alkyl, aralkyl or aryl linking ligands can also have as one functional group either a primary or secondary amino or thiol group and as the other functional group either an OH or carboxyl group. Therefore, OH or carboxyl functions can be placed on the surface of a membrane and used either directly to covalently bind peptides or proteins, or the function can be used for a defined secondary derivatization prior to peptide or protein binding.

Although many of the examples presented above show only bifunctional compounds, it must be pointed out that compounds such as polyvinylamine and polyethyleneimine can provide oligo- or polyfunctionality to the membranes.

When the above nucleophiles are used to derivatize materials such as PVDF, the reaction can be of many types. For example, the derivatization can occur under strong alkaline conditions using inorganic bases. Alternately, the reaction can utilize a phase transfer catalyst, or in the preferred embodiment, the reaction can use the aminoor thiol-substituted compound itself to avoid or minimize membrane colorization and brittleness. If the nucleophile is deposited onto the membrane surface via hydrophobic or dipole/dipole interactions, the reaction should proceed under generally mild conditions.

When nucleophiles having both amino and thiol functions are contacted with PVDF, the thiol functions react to bind the nucleophile to the membrane surface, thereby allowing the amino functions to remain free for the coupling of the peptide or protein to the membrane. This coupling can be achieved using a variety of methods. In the first method, carboxyl groups within the peptide or protein can be reacted with the amino groups using carbodiimides (preferably those which are water-soluble). Alternately, carboxyl groups can be introduced onto the surface of the membrane via a reaction with an omega-thiol-substituted carboxylic acid such as, for example, thioglycolic acid. In this case, the amino groups within the peptide or protein are reacted with the carboxyl-substituted membrane using carbodiimides.

In the most preferred embodiment of the invention, an isothiocyanate function is used to derivatize membranes having amino functionalities to thereby provide membranes which covalently link the amino functions within a peptide or protein to the amino functions on the membrane. This can be easily accomplished by reacting the amino-functionalized membranes with diisothiocyanates. A variety of diisothiocyanates can be used, including but not limited to alpha,omega-alkyl diisothiocyanates having 2-10 carbon atoms in the alkyl chain (such as 1,6-diisothiocyanatohexane); aralkyldiisothiocyanates having 1-10 carbon atoms in the alkyl chain and up to three phenyl rings attached (such as 2-isothiocyanato-(4-isothiocyanato-phenyl) ethane; and aryldiisothiocyanates having a variable number of hydrogen atoms replaced by nitrogen, halogens and cyanogens. Representative aryldiisothiocyantes include 1,4-phenylenediisothiocyanate and 2,5-dichloro-1,4-phenylene diisothiocyanate.

A variety of representative reactions of the type described above are provided in FIG. 1(a)-1(e).

In FIG. 1(a), a first polyvinylidene difluoride (PVDF) membrane is reacted with an alkyl diamine having 2-20 carbon atoms on the alkyl chain. The reaction product is then reacted with a diisothiocyanate such as 1,4-phenylenediisothiocyanate to provide a first, fully-derivatized PVDF membrane for covalently binding peptides and proteins. The 1,4-phenylenediisothiocyanate has groups $R_1$, $R_2$, $R_3$ and $R_4$ which are each independently selected from the group consisting of hydrogen, nitrogen, halogens and cyanogens.

Figure 1B:
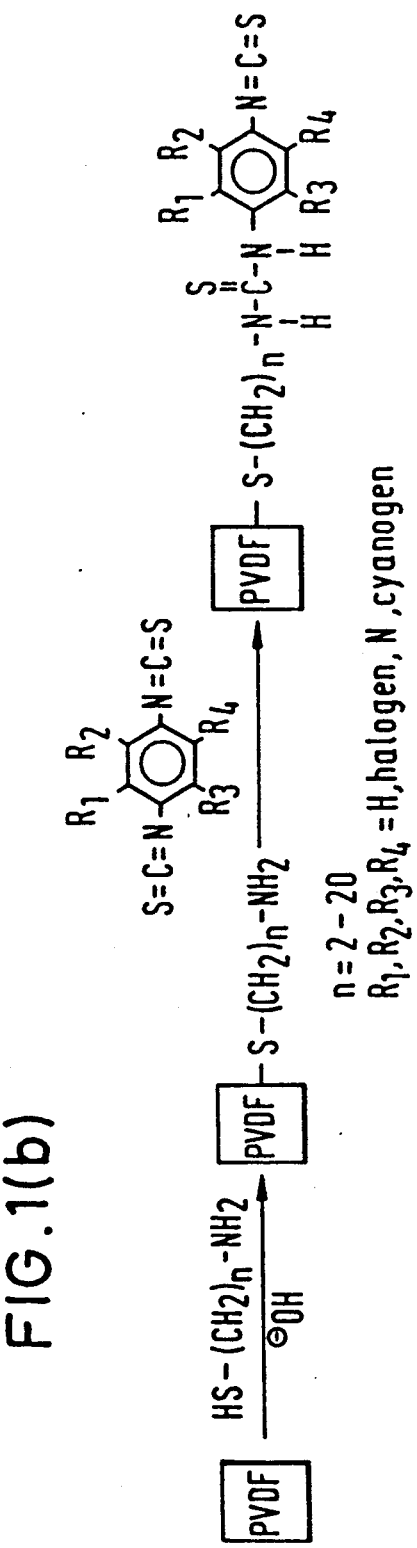

In FIG. 1(b), a second PVDF membrane is reacted with a thioaminoalkane having 2-20 atoms on the alkyl chain. The reaction product is reacted with the diisothiocyanate of FIG. 1(a) to provide a second, fully-derivatized PVDF membrane for covalently binding peptides and proteins.

Figure 1C:
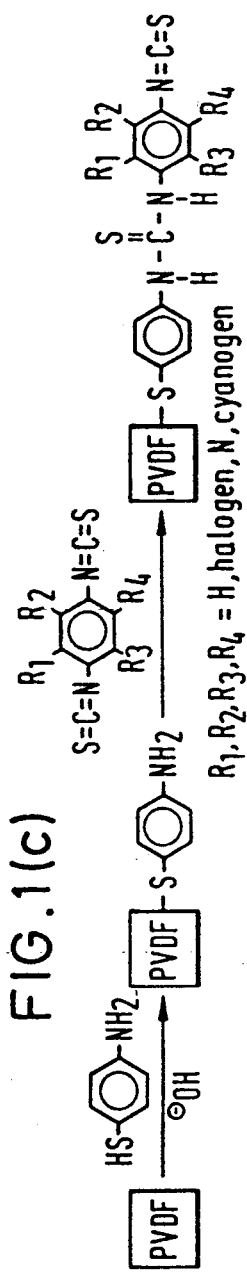

In FIG. 1(c), a third PVDF membrane is reacted with a thioaminobenzene. The reaction product is useful for the direct covalent attachment of peptides and proteins, or alternately, can be further reacted with the diisothiocyanate of FIG. 1(a) to provide a third, fully-derivatized PVDF membrane for covalently binding peptides and proteins.

Figure 1D:
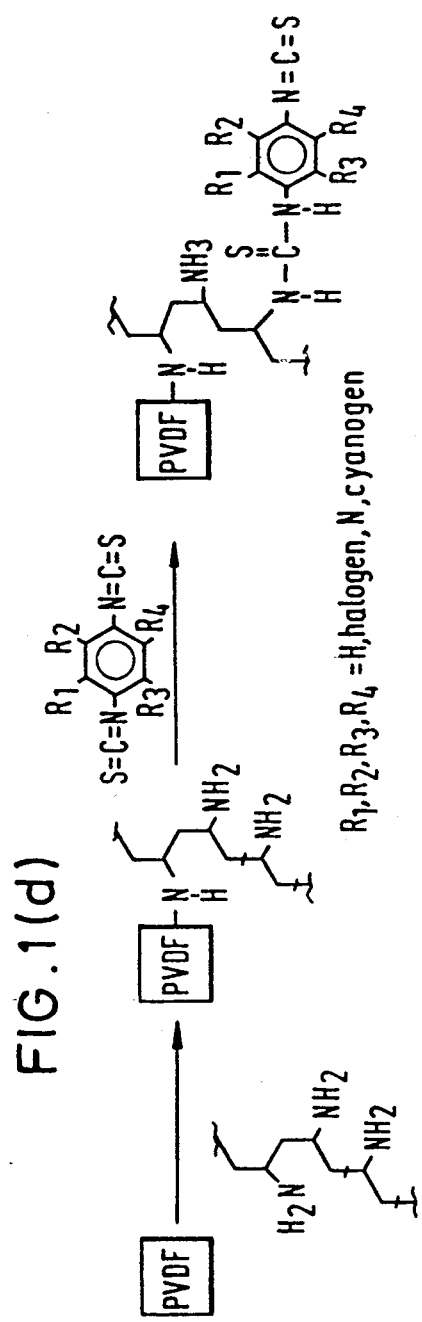

In FIG. 1(d), a fourth PVDF membrane is reacted with a polyvinylamine. The reaction product is reacted with the diisothiocyanate of FIG. 1(a) to provide a fourth, fully-derivatized PVDF membrane for covalently binding peptides and proteins.

Figure 1E:
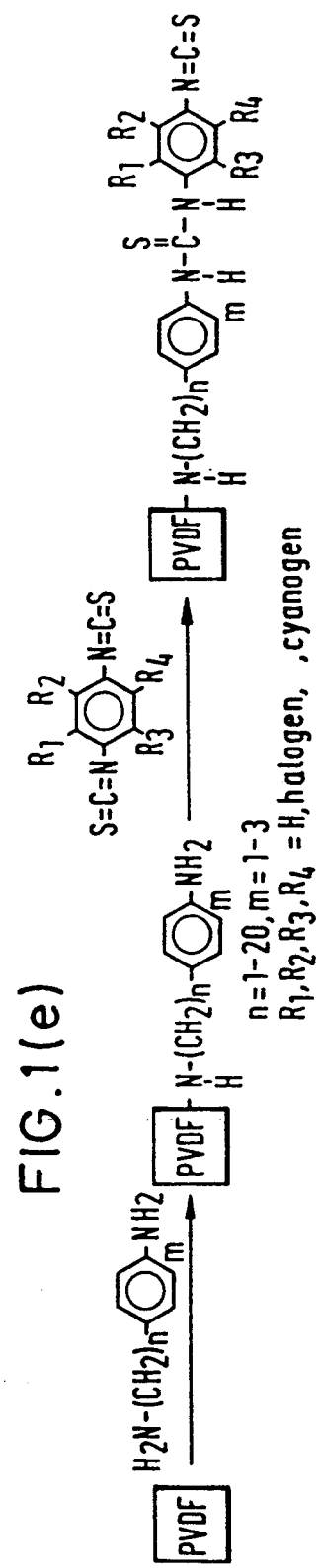

In FIG. 1(e), a fifth PVDF membrane is reacted with a diamino aralkane having 1-20 carbon atoms on the alkyl chain and 1-3 phenylene groups. The reaction product is useful for the direct covalent attachment of peptides and proteins, or alternately, can be further reacted with the diisothiocyanate of FIG. 1(a) to provide a fifth, fully-derivatized PVDF membrane for covalently binding peptides and proteins.

Functional groups suitable for covalently binding peptides and proteins can be introduced onto the surface of coated membranes by a variety of methods. In a preferred embodiment, as represented in FIG. 2, the coating is hydroxylated, thereby providing an —OH function on the surface thereof. The hydroxylated coating is then activated with a material such as 1,1'-carbonyldiimidazole (CDI) and subsequently derivatized as previously described. As before, a wide variety of nucleophiles are suitable for the derivatization step including the amino and/or thio alkanes, aralkylamines and aralkylthiols, and arylamines and arylthiols previously described.

In a preferred embodiment, the —OH functional group on the membrane surface is derivatized in a manner which provides an amino functionality. This amino function can then be used to covalently link peptides and proteins to the membrane surface via their carboxylic groups using carbodiimides. In the most preferred embodiment, however, diisothiocyanates are used to further derivatize the membrane surface. This provides the surface with an isothiocyanate functionality which can covalently link the membrane surface to peptides and proteins via their amino groups.

Figure 2A:
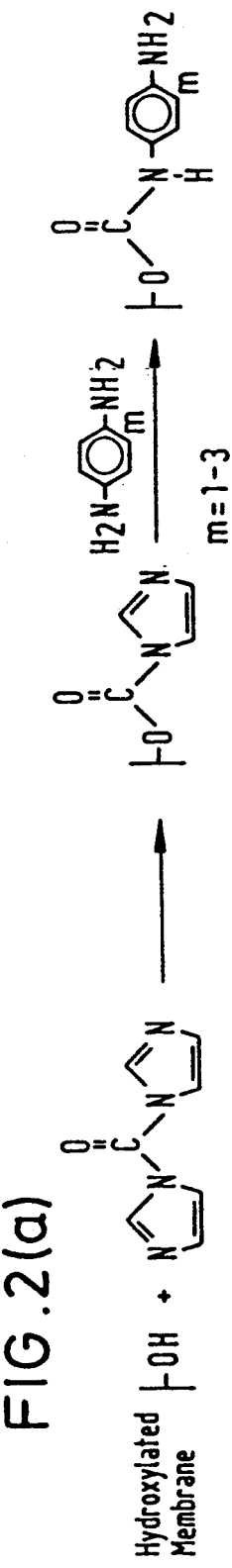
FIG. 2 presents representative formulae for the derivatization of coated membranes to provide coated membranes suitable for covalently binding peptides and proteins.
Figure 2B:
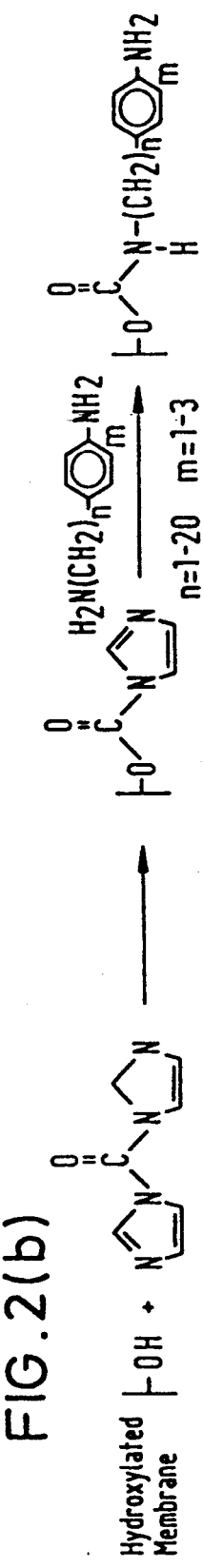
Figure 2C:
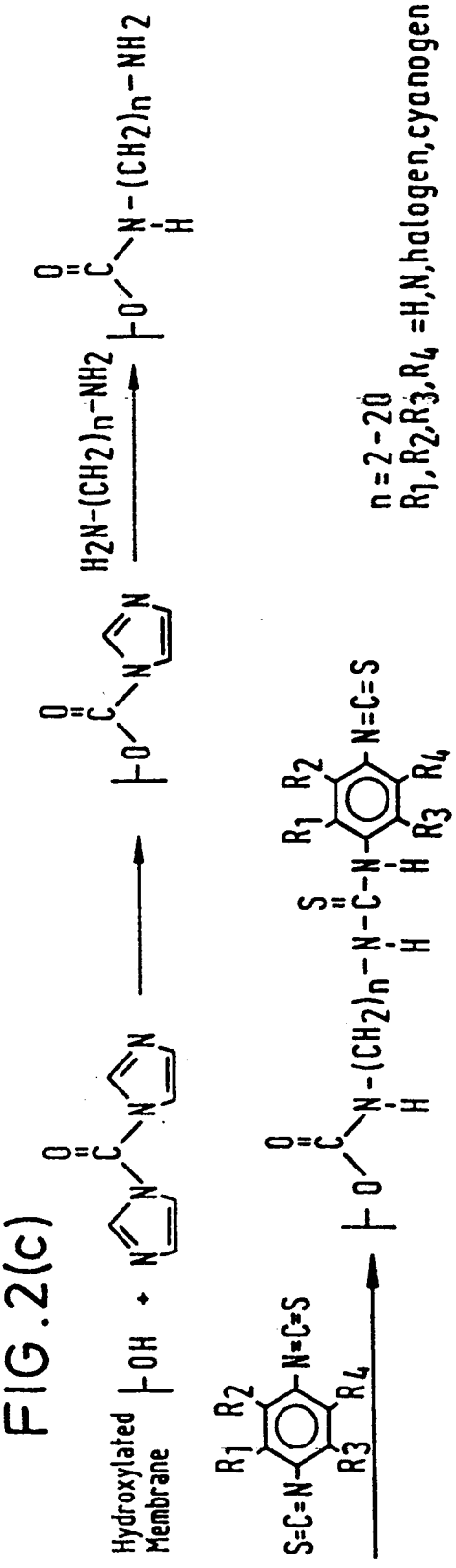

Representative membrane derivatization reactions are presented in FIG. 2(a)-2(c).

In FIG. 2(a), a first hydroxylated membrane surface is activated with CDI. This CDI-activated surface is then reacted with an aryl diamine having 1-3 phenylene groups. The phenylene groups can be either substituted or unsubstituted in the ortho and/or meta positions. The resulting surface is useful for the direct covalent attachment of peptides and proteins, or alternately, can be further reacted with a diisothiocyanate as shown in FIG. 1(a) to provide a first, fully derivatized, coated membrane for covalently binding peptides and proteins.

In FIG. 2(b), a second hydroxylated membrane surface is activated with CDI as in FIG. 2(a). This CDI-activated surface is then reacted with a diamino aralkane having 1-20 carbon atoms on the alkyl chain and 1-3 phenylene groups. The phenylene groups can be either substituted or unsubstituted in the ortho and/or meta positions. The resulting surface is useful for the direct covalent attachment of the peptides and proteins, or alternately, can be further reacted with a diisothiocyanate as shown in FIG. 1(a) to provide a second, fully derivatized, coated membrane for covalently binding proteins and peptides.

In FIG. 2(c), a third hydroxylated membrane surface is activated with CDI as shown in FIG. 2(a). This CDI-activated surface is then reacted the alkyl chain. The reaction product is then reacted with a diisothiocyanate as shown in FIG. 1(a) to provide a third, fully derivatized, coated membrane for covalently binding peptides and proteins.

The derivatized membranes described herein are useful for the manual or automated solid-phase sequencing of peptides and proteins. The sequence of a peptide or protein can be determined by a stepwise chemical or enzymatic degradation from either the N- or C-terminal end.

The proteins to be sequenced can be transferred from a separatory gel and covalently bound to the membrane either by direct blotting or by electroblotting subsequent to one- or two-dimensional electrophoresis. In either case, any chemical or enzymatic fragmentation and purification of the proteins or peptides can be performed under controlled conditions directly on the membrane surface. This provides a covalently-bound fragment, suitable for sequencing procedures, which has been immobilized in a direct and convenient process. Direct immobilization provides a process well-suited to automated sequencing methods.

By covalently binding proteins and peptides to the membrane surface during sequencing, a number of advantages can be achieved. Protein losses from the surface during sequencing are minimized thereby allowing determinations which remain highly effective despite repetitive sequencing cycles. Additionally, the covalent bonds allow the use of efficient chemistries and stringent washing steps between sequencing cycles, thereby reducing total sequencing time. The stringent washing also enables the use of highly sensitive sequencing methods and reduces the amount of chemical impurities that might interfere with the HPLC analysis of the PTH amino acids.

The use of functional groups for covalent attachment of peptides and proteins to a solid substrate is not intended to be restricted to any particular sequencing method. To the contrary, a variety of different solid-phase sequencing methods have been suggested in the art. The present invention is intended to have utility for any solid-phase, liquid-phase, gas-phase or multi-phase sequencing method in which the covalent attachment of peptides and proteins to a solid supporting matrix is desired.

In the preferred embodiment, however, the preferred sequencing process is the Edman sequencing process previously described. The present materials are particularly useful for this process since they can maintain both their physical and chemical properties despite the harsh chemical reagents employed during the Edman method.

The invention will now be more particularly pointed out in the following examples.

EXAMPLES

Example 1

Reaction of Polyvinylidene Difluoride Membranes with Amines

A. Five sheets of polyvinylidene difluoride (PVDF) membrane (13×13 cm, 0.45 u pore size), commercially available as Immobilon P transfer membrane from Millipore Corp., Bedford, Mass. were wet with 300 mL methanol. The methanol-wet material was placed in a dish of deionized water (500 mL) to effect removal of the methanol from the surface of the membrane. The water in the dish was drained and replaced with fresh deionized water at 2 minute intervals a total of 5 times. The water-wet membrane sheets were then immersed in 400 mL of a 0.1 M aqueous solution of 1,10-diaminodecane maintained at 75° C. Sheets of membrane were removed at 2.5, 4.0, 8.0, 12.0 and 24.0 minute intervals after immersion in the diamine solution. The membranes were placed in a dish containing 500 mL of methanol. The methanol in the dish was drained and replaced with fresh methanol (250 mL) at 5 minute intervals a total of 4 times. The membrane sheets were then dried in vacuo. A picric acid binding assay was used to determine the amount of amino groups that were present on the membrane surface. Picric acid binding assays were performed by accurately weighing out a piece of membrane (5 mg) and treating it with a 0.2 M solution of picric acid in dichloromethane. The membrane fragment was washed with dichloromethane and placed in 10.0 ml of freshly prepared 4% triethylamine in dichloromethane for 20 minutes. The absorbance of the desorbed triethlammonium picrate was recorded at 358 nm ($E358 = 14,500$). The results are given in Table I below:

TABLE I

| Reaction Time (min) | umol $NH_2$/g Membrane |
| --- | --- |
| 2.5 | 5.8 |
| 4.0 | 6.6 |
| 8.0 | 6.8 |
| 12.0 | 7.0 |
| 24.0 | 7.5 |

B. A sheet of polyvinylidene difluoride membrane (13×13 vm, 0.45 u pore size), commercially available as Immobilon P transfer membrane from Millipore Corp. Bedford, Massachusetts was wet with 100 mL of methanol and placed in a dish of deionized water (500 mL). The water in the dish ws drained and replaced every 2 minutes a total of 5 times. The membrane sheet was then immersed for 24 minutes in 100 mL of a 0.1 M aqueous solution of 2-(4-aminophenyl)ethylamine maintained at 55° C. The sheet was removed from the amine solution and placed in a dish containing 100 mL of methanol. The methanol was drained and replaced with fresh methanol every 5 minutes a total of 4 times. Following the last methanol wash, the sheet was dried in vacuo. The picric acid binding assay described in Example 1, Part A revealed the material contained about 2.4 umol of amino groups per gram of dry membrane.

C. Five sheets of polyvinylidene difluoride membrane (13×13 Cm, 0.45 u pore size), Commercially available as Immobilon P transfer membrane from Millipore Corp., Bedford, Massachusetts were wet with 300 mL methanol. The methanol wet material was placed in a dish of deionized water (500 mL) to effect removal of the methanol from the surface of the membrane. The water in the dish was drained and replaced with fresh deionized water at 2 minute intervals a total of 5 times. The water wet membrane sheets were then immersed in 200 mL of a 2% (w/v) solution of polyvinylamine in 5% aqueous (w/v) sodium carbonate maintained at 90.C. The sheets were removed after 10 minutes and placed in a dish containing 500 mL of methanol. The methanol in the dish was drained and replaced with fresh methanol (250 mL) at 5 minute intervals a total of 4 times. The membrane sheets were then dried in vacuo. The picric acid binding assay described in Example 1, Part A was used to determine the amount of amino groups that were present on the membrane surface. The material contained about 10.7 umol of amino groups per gram of dry membrane.

D. Three sheets of polyvinyldene difluoride membrane (10 cm×30 cm, 0.45 u pore size), commercially available as Immobilon P transfer membrane from Millipore Corp., Bedford, Massachusetts were wet with methanol. The methanol-wet material was placed in a dish of deionized water (500 mL) to effect removal of the methanol from the surface of the membrane. The water-wet membrane sheets were then immersed in 200 mL of 30% (v/v) aqueous ethylene diamine containing 1% (v/v) of 55% aqueous tetrabutylammonium hydroxide for five minutes. The sheets were removed from the ethylene diamine solution and heated for intervals of 1, 2 or 3 minutes at 85° C. on a rotary film dryer. Following heating, the sheets were washed extensively with deionized water and dried in vacuo. The picric acid binding assay described in Example 1, Part A was used to determine the amount of amino groups that were present on the membrane surface. The results are given in Table II below:

TABLE II

| Time of Heating (min) | umol $NH_2$/g Membrane |
| --- | --- |
| 1 | 8.0 |
| 2 | 11.0 |
| 3 | 13.5 |

Example 2

Reaction of Polyvinylidene Difluoride Membranes with Thiols

A. A 3×1 cm piece of polyvinylidene difluoride membrane (0.45 u pore size), commercially available as Immobilon P transfer membrane from Millipore Corp., Bedford, Massachusetts was wet with methanol and placed in a dish containing 25 mL of deionized water. The deionized water was replaced every 2 minutes, a total of 5 times. The membrane piece was immersed for 35 minutes in a solution containing 2.0 mmole of 4-aminothiophenol and 2.5 mmol of triethylamine in 4.0 mL of deionized water at 65° C. The membrane was washed with methanol and dried in vacuo. The picric acid binding assay (described in Example 1, Part A) revealed the material contained about 4.1 umol of amino groups per gram of dry membrane.

B. Seven 1 cm×4 cm pieces of polyvinylidene difluoride membrane, (0.45 u pore size), commercially available as Immobilon P transfer membrane from Millipore Corp., Bedford, Massachusetts, were wet with methanol and placed in a dish containing 25 mL of deionized water. The deionized water was replaced every 2 minutes, a total of 5 times. The membrane pieces were immersed in a room temperature solution of 2.0 g of sodium hydroxide and 2.5 g of 2-aminoethanethiol hydrochloride in 10.5 ml of 40% aqueous ethanol. The membrane pieces were removed from the solution at various times and washed with deionized water. Following washing with methanol the pieces were dried in vacuo. The picric acid binding capacity (described in Example 1, Part A) of each piece was determined, and the results are given in Table III below:

TABLE III

| Reaction Time (min) | umol $NH_2$/g Membrane |
| --- | --- |
| 16 | 3.7 |
| 33 | 4.4 |
| 48 | 4.5 |
| 110 | 6.1 |
| 169 | 8.3 |
| 212 | 8.7 |
| 251 | 10.3 |

Example 3

Synthesis of Amine-Modified Hydrophilic Membranes

A. Eight 15.5 cm×19 cm pieces of 2-hydroxypropylacrylate-coated polyvinylidene difluoride membrane (0.65 u pore size), described in U.S. Pat. No. 4,618,533 discussed previously and available as DVPP membrane from Millipore Corp., Bedford, Mass., were placed for sixteen hours at room temperature in 40 ml of acetone containing 2.0 g of 1,1'-carbonyl diimidazole. Subsequently, the membrane was washed with acetone and dried in vacuo.

B. Three 15.5 cm×19 cm pieces of the above activated membrane (described in Example 3, Part A) were placed in 20 ml of a solution of 0.5 M 1,4-phenylenediamine in acetone for sixteen hours at room temperature. The membrane pieces were washed with acetone and dried in vacuo. The picric acid binding assay (described in Example 1, Part A) revealed that the material contained about 139 umol of amino group per gram of dry membrane.

C. Three 15.5 cm×19 cm pieces of the above activated membrane (described in Example 3, Part A) were placed in 20 ml of a solution of 0.5 m 2-(4- aminophenyl)-ethyl amine in acetone for sixteen hours at room temperature. The membrane peices were washed with acetone and dried in vacuo. The picric acid binding assay (described in Example 1, Part A) revealed that the material contained about 130 umol of amino group per gram of dry membrane.

D. Two 15.5 cm×19 cm pieces of the above activated membrane (described in Example 3, Part A) were placed in 20 ml of a solution of 0.5 m 1,3-diamino propane in acetone for sixteen hours at room temperature. The membrane pieces were washed with acetone and dried in vacuo. The picric acid binding assay (described in Example 1, Part A) revealed that the material contained about 132 umol of amino groups per gram of dry membrane.

Example 4

Synthesis of Isothiocyanate Functionalized Membranes

Sheets of amino functionalized PVDF membranes, as derivatized in Example 1, Parts A, C and D; Example 2, Part B; and Example 3, Part D, were immersed in a 0.5 M solution of 1,3-phenylene diisothiocyanate (DITC) or 2,5-dichloro-1,4-phenylene diisothiocyanate (DCDITC) in dry tetrahydrofuran (THF) at room temperature. After 3 hours the sheets were washed with dry THF, followed by methanol. The membranes were dried in vacuo and stored −20° C. with the exclusion of moisture. Samples of the various membranes were assayed for the presence of amino groups using the previously described picric acid binding assay. The yield of the reaction was calculated from the loss of assayable amine groups on the membrane surface. The results are given in Table IV below:

TABLE IV

| Example | Starting Membrane | Isothiocyanate (concentration (M)) | umol NH$_2$/g Before Reaction | umol NH$_2$/g After Reaction | Yield |
|---|---|---|---|---|---|
| 4A | 1A | DITC (0.5) | 6.4 | 2.4 | 62% |
| 4B | 1A | DCDITC (0.5) | 6.4 | 1.1 | 81% |
| 4C | 1C | DITC (0.5) | 10.7 | 2.1 | 80% |
| 4D | 1C | DCDITC (0.5) | 10.7 | 2.5 | 77% |
| 4E | 1D | DITC (0.5) | 13.5 | 6.0 | 55% |
| 4F | 2B | DCDITC (0.1) | 50.7 | 7.7 | 85% |
| 4G | 3D | DITC (0.5) | 132.0 | 20.0 | 85% |

Example 5

Sequence Analysis of Proteins Covalently Attached to Isothiocyanate Functionalized Membranes A. A membrane disc (11.5 mm diameter) as given in Example 4(G) was wet with methanol and washed with deionized water. The water-wetted disc was then immersed in 0.2 mL of 0.2 M sodium phosphate buffer (pH 8.8) containing 0.25% (w/v) sodium dodecyl sulphate and 200 pmol of horse heart myoglobin (Type III; Sigma Chemical Company, St. Louis, MO). The disc was incubated in this solution for 30 minutes at 55° C. (under argon) then washed with deionized water containing 0.05% (v/v) n-propylamine.

The membrane disc was then placed directly in the reaction chamber of an automated solid-phase sequencer (Model 8500, Milligen, Division of Millipore Corp., Bedford, Mass.) and subjected to 30 cycles of solid-phase Edman degradation essentially as described by R.A. Laursen, *Eur. J. Biochem.*, 20:89 (1971). An important feature of this implementation of the Edman degradation chemistry is that all the reagents and solvents are delivered into the reaction chamber as liquid solutions, including the cleavage acid (TFA). Any protein or peptide material that had failed to bind covalently to the isothiocyanate derivatized membrane would elute from the reaction chamber to waste.

The cleaved anilinothiazolinone (ATZ) amino acids were converted to the corresponding phenylthiohydantoin (PTH) derivatives by incubation in 30% (v/v) aqueous trifluoracetic acid (TFA) for 16 minutes at 70° C. The PTH amino acids were identified by reversed-phase high-pressure liquid chromatography (HPLC) on a 30 cm × 3.9 mm 5 micron 'Resolve' C-18 column (Millipore Corporation, Waters Chromatography Division, Milford, Mass.) using a method derived from Zimmerman et al., *Analyt. Biochem.*, 77:569 (1977). The chromatography equipment comprised a Waters 600E fluid pumping system, Waters model 712D autosampler and Waters model 490 UV/Vis detector. PTH amino acids were quantified at 269 nm using a Waters 820 chromatography workstation and 'Maxima' data analysis software. Serine and Threonine residues were confirmed by the appearance of their beta elimination products monitored at 313 nm.

The sequence data was reduced to a semilog plot of Log[PTH yield] versus Cycle no., with the line fitted by regression analysis. The result is presented in FIG. 3(a). For this sample the initial sequencing yield was 97.6 pmol (corresponding to 48% of the initial sample) and the average repetitive sequencing yield (derived from the slope of the fitted line) was 94.8%.

B. A membrane disc (11.5 cm diameter) as given in Example 4(E) was wet with methanol and washed with deionized water. The water-wetted disc was then placed on a double layer of Whatman no. 4 filter paper (Whatman Limited, Maidstone, U.K.) and lightly pressed onto the paper surface to remove excess water. 300 pmol of a bacterial monooxygenase gamma subunit in 15 ul 0.2 M Na phosphate buffer (pH 8.8) containing 0.25% (w/v) sodium dodecyl sulphate was then pipetted directly onto the membrane surface and the droplet of liquid allowed to blot through the membrane disc over some 10–15 seconds by capillary action. This 'dot blot' process utilizes the protein binding characteristics of the base PVDF membrane to non-covalently adsorb protein from aqueous solution as it passes through the membrane (see N. LeGendre and P. Matsudaira, *Biotechniques*, 6 154, 1988). The membrane disc was then warmed to 50 C for 20 minutes to allow the protein to react covalently with the isothiocyanate groups, placed directly in the sequence reaction chamber and sequenced for 30 cycles as described above. Examples of the raw HPLC traces are shown in FIG. (a)–(f), clearly demonstrating the very low background level of UV absorbing materials that might interfere with identification of the PTH amino acid in each cycle.

Figure 3B:
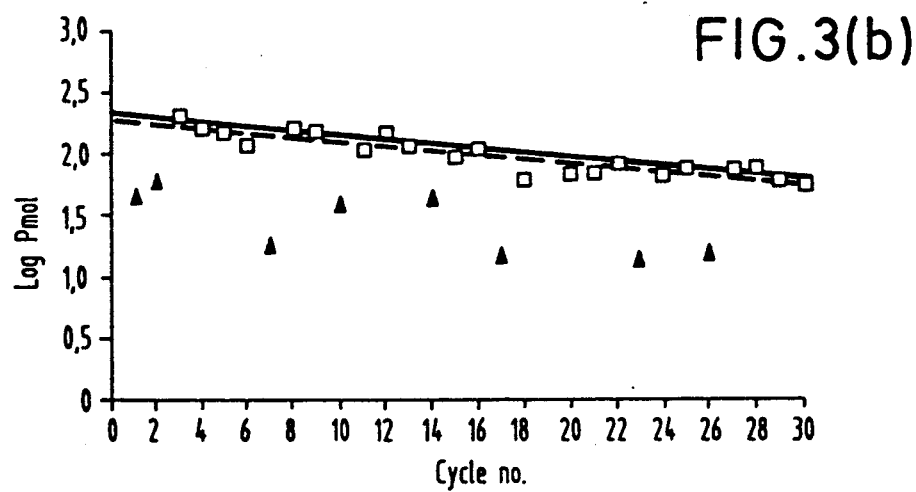
Figure 4A:
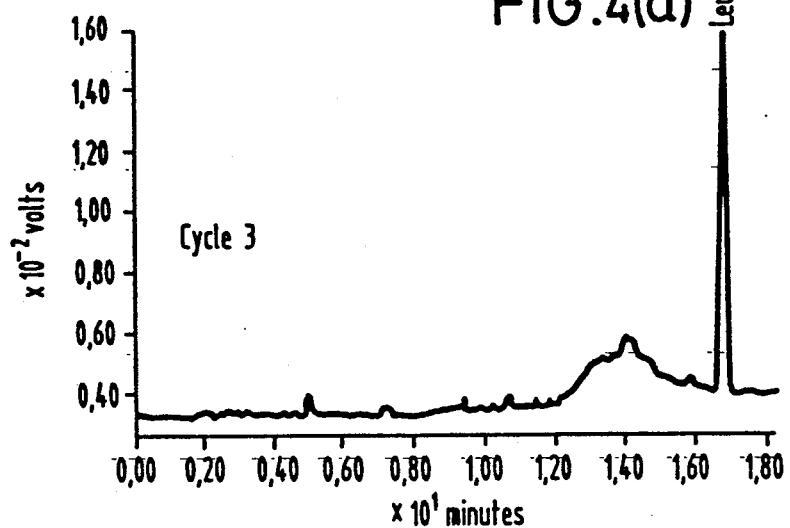
FIG. 4 presents representative sequence cycle data from the solid-phase sequence analysis of a protein covalently bound to a representative membrane of the invention.
Figure 4B:
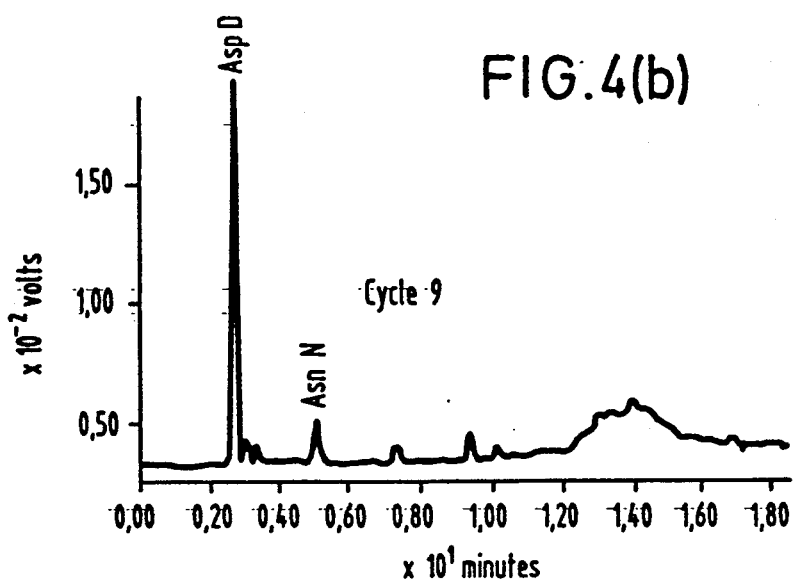
Figure 4C:
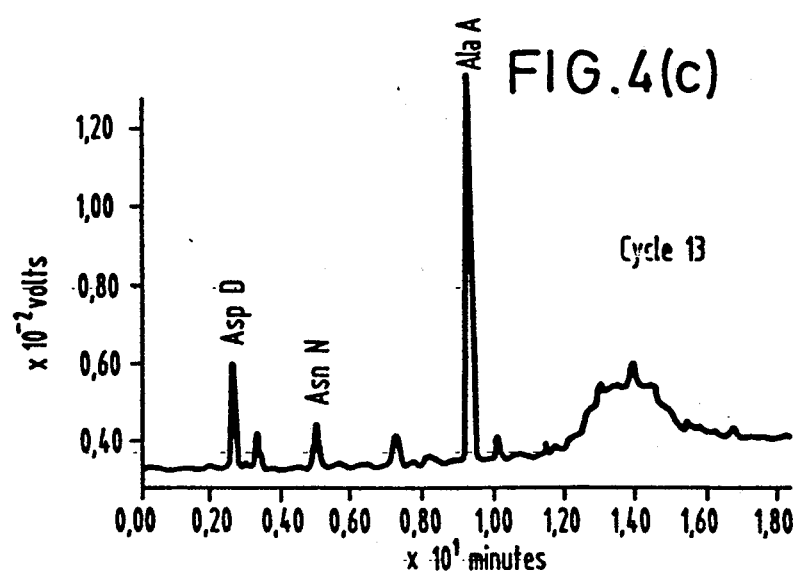

FIG. 4(a)–(f) presents representative sequencer cycle data from the solid-phase sequence analysis of bacterial monooxygenase gamma subunit coavlently bound to DITC activated PVDF. FIG. 4(a) Sequencer cycle 3; Leucine, 141 pmol. FIG. 4(b): Sequencer cycle 9; Aspartic acid, 101 pmol. FIG. 4(c): Sequencer cycle 13; Alanine, 77 pmol. FIG. 4(d): Sequencer cycle 19; Alanine, 55 pmol. FIG. 4(e): Sequencer cycle 25; Glutamic acid, 48 pmol. FIG. 4(f): Sequencer cycle 28; Alanine, 50 pmol. HPLC analyses shown comprise 62.5% of total recovered PTH fraction. A semilog plot of Log[PTH yield] versus cycle no. is also included as FIG. 3(b). The initial sequencing yield was 207 pmol (corresponding to 69% of the initial sample) and the average repetitive sequencing yield was 95.9%.

C. 2 mg of horse heart myoglobin (Type III; Sigma Chemical Corp.) was dissolved in 2 ml of 10 mM Tris.glycine buffer (pH 8.3) containing 1% (v/v) beta mercaptoethanol and boiled for 2 minutes. A small aliquot (10 ul) was then subjected to gradient SDS polyacrylamide gel electrophoresis (16 cm × 12 cm × 0.15 cm gel; 10–20% acrylamide gradient; running buffer comprising 25 mM Tris, 192 mM glycine, 0.1% (w/v) SDS; electrophoresis for 4 hours at 70 milliamp constant current; tank buffer cooled to 20° C.). The protein sample was recovered from the SDS gel by electroblotting onto a DITC activated PVDF sheet (10 cm × 10 cm) as in Example 4(E) using a Transphor Electroblot apparatus (Hoefer Scientific Instruments, San Francisco, CA). The SDS gel was first pre-equilibrated for 15 minutes in the transfer buffer (25 mM Tris, 192 mM glycine, 10% (v/v) methanol) then electroblotted for 1.25 hours at 60

V with the tank buffer cooled to 20° C. The blotted protein was visualized by staining the membrane with stainsall (a coloured cationic dye) according to the method of M. R. Green et al., *Analyt. Biochem.*, 56:43 (1973). An 11.5 mm disc encompassing the stained protein band was excised from the membrane sheet, placed directly in the sequencer reaction chamber and subjected to 30 cycles of automated solid-phase Edman degradation as described above. A semilog plot of Log[PTH yield] versus Cycle no. is presented in FIG. 3(c). The initial sequencing yield was 73 pmol; the average repetitive sequencing yield was 93.8%.

Figure 3A:
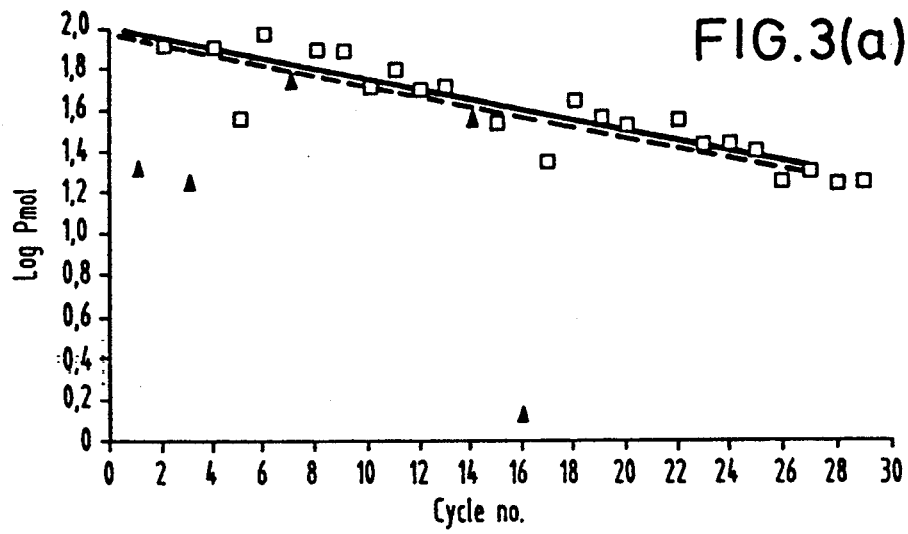
FIG. 3 presents sequence data in the form of semilog plots of Log (PTH yield) versus cycle number for sequence determinations of proteins immobilized on representative membranes of the invention.
Figure 3C:
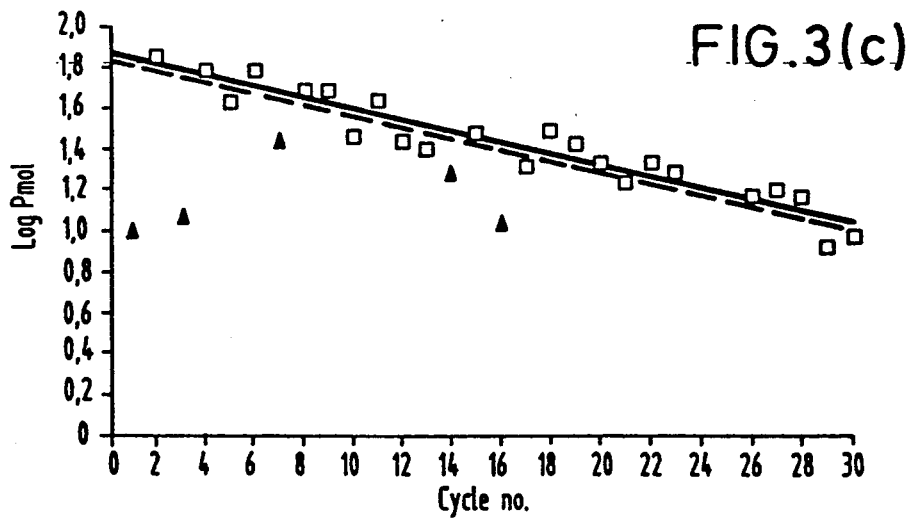

For each of the samples described in Examples 5(A) to 5(C) and presented in FIG. 3(a)-(c), the sequence data was reduced to a semilog plot of Log[PTH yield]versus Cycle no. and the lines fitted by regression analysis. PTH amino acid residues that are partially destroyed or recovered in reduced yield due to the coupling or ATZ to PTH conversion procedures (Ser, Thr, Trp, Cys, Lys) were not included in the regression analysis (▲). Initial sequencing yields were derived from the intercept of the Y-axis. Average repetitive sequencing yields were obtained by taking the antilog of the slope of the fitted line.

(D) A membrane disc (11.5 cm diameter) as in Example 4(A) was wet with methanol and washed with deionized water. The disc was then immersed in 0.3 ml 0.1 M sodium carbonate buffer (pH 10.5) containing 0.25% (w/v) SDS and 300 pmol horse heart myoglobin (Type III; Sigma Chemical Corp.). The disc was incubated in the solution for 30 minutes at 55° C. (under argon) then washed with water containing 0.05% (v/v) n-propylamine. The membrane disc was then placed directly in the sequencer reaction chamber and subjected to 16 cycles of automated solid-phase Edman degradation as described above. The initial sequencing yield was 98 pmol (corresponding to 33% of the initial sample) and the repetitive yield was 93.5%.

Equivalents Those skilled in the art will recognize or be able to ascertain using no more than routine experimentation many equivalents to the specific embodiments described herein. Such equivalents are intended to be encompassed by the following claims.

We claim:

1. A flexible, polymeric, porous membrane suitable for use with solid phase protein sequencing processes, said membrane having functional groups that covalently link peptides and proteins to the membrane surface.

2. A membrane as in claim 1 wherein said functional groups are selected from the group consisting of —NH$_2$, —SH, —OH, —COOH, isothiocyanates and combinations thereof.

3. A membrane as in claim 1 having —NH$_2$ functional groups reacted with diisothiocyantes to thereby provide a derivatized membrane capable of covalently binding peptides and proteins.

4. A membrane as in claim 1 comprising a polymeric fluorocarbon.

5. A membrane as in claim 4 wherein the polymeric fluorocarbon comprises polyvinylidene difluoride.

6. A membrane as in claim 1 comprising a plastic material coated with a crosslinked polymer suitable for covalently binding peptides and proteins either directly or after further chemical derivatization.

7. A membrane as in claim 6 wherein the crosslinked polymer has an —OH functionality.

8. A membrane as in claim 1 in which the functional groups are provided by a nucleophile, said nucleophile having a first functional group capable of binding to the membranesurface or a coating thereon, a second functional group capable of covalently binding peptides and proteins or capable of being derivatized to covalently bind peptides and proteins, and an organic linking radical to link the first and second functional groups.

9. A membrane as in claim 8 wherein the first functional group is selected from the group consisting of —NH$_2$, —SH, —OH and —COOH.

10. A membrane as in claim 8 wherein the second functional group is selected from the group consisting of —NH$_2$, —SH, —OH, —COOH and isothiocyanates.

11. A membrane as in claim 6 wherein the organic linking radical is selected from the group consisting of alkyl radicals, aralkyl radicals and aryl radicals.

12. A membrane as in claim 8 wherein the nucleophile contains more than two functional groups.

13. A membrane as in claim 8 wherein the nucleophile is selected from the group consisting of 1,2-diaminoethane, 1,10-diaminodecane, 2-(4-aminophenyl)ethylamine, 2-(4-aminophenyl)phenetheylamine, 6-(4-aminophenyl) hexylamine 1,4-diaminobenzene, 1,6-dithiohexane, 2-thio(4-thiophenyl)ethane, 1,4-dithiobenzene, 2-amino-1-thioethane, 2-(4-thiophenyl)ethylamine, 2-thio(4-aminophenyl) ethane, 4-aminothiophenol, polyvinylamine and polyethyleneimine.

14. A membrane as in claim 1 having a peptide or protein immobilized thereon, said peptide or protein being covalently linked to the membrane by the functional groups.

15. A flexible, porous membrane suitable for use with solid phase protein sequencing processes, said membrane comprising polyvinylidene difluoride having isothiocyanate functional groups thereon.

16. A flexible, porous membrane suitable for use with solid phase protein sequencing processes, said membrane comprising polyvinylidene difluoride having a coating which comprises a crosslinked hydroxypropyl acrylate, said coating having isothiocyanate functional groups thereon.

* * * * *

UNITED STATES PATENT AND TRADEMARK OFFICE
CERTIFICATE OF CORRECTION

PATENT NO. : 5,011,861

DATED : April 30, 1991

INVENTOR(S) : James M. Coull, Darryl J.C. Pappin, Hubert Koester, Malcolm G. Pluskal, Michael J. Steuck, Alex G. Bonner It is certified that error appears in the above-identified patent and that said Letters Patent is hereby corrected as shown below:

Title page, Inventors' Names, please change "Darryl J. Rappin" to --- Darryl J.C. Pappin ---.

Signed and Sealed this

Twenty-fourth Day of December, 1991

Attest:

HARRY F. MANBECK, JR.

Attesting Officer

Commissioner of Patents and Trademarks